United States Patent [19]

Kralovic et al.

[11] Patent Number: 5,350,563
[45] Date of Patent: Sep. 27, 1994

[54] COLD STERILANT WITH EXTENDED ACTIVE LIFE

[75] Inventors: Raymond C. Kralovic, Willoughby; David Z. Levin, Mayfield Heights; Lorraine D. H. Lindeman, Mentor, all of Ohio

[73] Assignee: Steris Corporation, Mentor, Ohio

[21] Appl. No.: 90,791

[22] Filed: Jul. 12, 1993

Related U.S. Application Data

[63] Continuation-in-part of Ser. No. 64,391, May 18, 1993, which is a continuation-in-part of Ser. No. 23,048, Feb. 25, 1993, which is a continuation-in-part of Ser. No. 793,589, Nov. 18, 1991, Pat. No. 5,209,909, which is a continuation-in-part of Ser. No. 681,118, Apr. 5, 1991, Pat. No. 5,217,698, and Ser. No. 342,189, Apr. 24, 1989, Pat. No. 5,116,575, said Ser. No. 681,118, is a continuation-in-part of Ser. No. 349,304, May 9, 1989, Pat. No. 5,091,343, and Ser. No. 342,189, May 9, 1989, said Ser. No. 349,304, is a continuation-in-part of Ser. No. 140,388, Jan. 4, 1988, Pat. No. 4,892,706, said Ser. No. 342,189, is a continuation-in-part of Ser. No. 229,917, Aug. 8, 1988, Pat. No. 5,077,008, which is a continuation-in-part of Ser. No. 140,388, Aug. 8, 1988, and Ser. No. 165,189, Mar. 7, 1988, Pat. No. 5,037,623, which is a continuation-in-part of Ser. No. 826,730, Feb. 6, 1986, Pat. No. 4,731,222, said Ser. No. 140,388, is a continuation-in-part of Ser. No. 826,730, Feb. 6, 1986.

[51] Int. Cl.$^5$ .............................................. C11D 7/12
[52] U.S. Cl. ............................................. 422/28; 422/16; 252/99; 252/174.14; 252/174.19
[58] Field of Search .................. 422/16, 28, 292, 293; 134/60, 94, 100; 252/99, 103, 174.14, 174.19

[56] References Cited

U.S. PATENT DOCUMENTS 5,015,408  5/1991  Reuss .................................. 252/99
5,116,575  5/1992  Badertscher et al. ................ 422/28

OTHER PUBLICATIONS

"Desinfectant Effect of Persteril In Combination With Detergents/", V. Melicherčíková, Journal of Hygiene, Epidermiology, Microbiology and Immunology, 33, 1989, No. 1, 19–28.

"Studies Conerning the Mechanism of Bleaching Activation", Hauthal et al., Tenside Surf. Det., 27, (1990), 3, pp. 187–193.

"Effect of pH on Sproicidal and Microbicidal Activity of Buffered Mixtures of Alcohol and Sodium Hypochlorite", Death, et al., J. of Clinic Pathology, 1979, 32, 148–153.

Primary Examiner—Lyle A. Alexander
Attorney, Agent, or Firm—Fay, Sharpe, Beall, Fagan, Minnich & McKee

[57] ABSTRACT

Sodium perborate is mixed with a mixture, preferably a 1:1 mixture, of a rapid acetylating agent, e.g. TAED, and a slow acetylating agent, e.g. acetylsalicylic acid, in water to form a biocidally effective peracetic acid solution. When sodium perborate and TAED alone react in water, peracetic acid is produced quickly but has relatively little stability and a short useful life (curve 10). When sodium perborate and acetylsalicylic acid are mixed in water, the peracetic acid solution takes an extended duration to reach maximum efficacy, but is stable for an extended duration (curve 12). The mixture of rapid and slow acetylating agents quickly produces a stable peracetic acid concentration (curve 14).

19 Claims, 2 Drawing Sheets

COLD STERILANT WITH EXTENDED ACTIVE LIFE

The present application is a continuation-in-part of U.S. patent application Ser. No. 08/064,391, filed May 18, 1993 which is a continuation-in-part of U.S. patent application Ser. No. 08/023,048, filed Feb. 25, 1993 which is a continuation-in-part of U.S. patent application Ser. No. 07/793,589, filed Nov. 18, 1991 now U.S. Pat. No. 5,209,909. U.S. patent application Ser. No. 07/793,589 is a continuation-in-part of U.S. patent application Ser. No. 07/681,118, filed Apr. 5, 1991, now U.S. Pat. No. 5,217,698, and U.S. patent application Ser. No. 07/342,189, filed Apr. 24, 1989, now U.S. Pat. No. 5,116,575.

U.S. patent application Ser. No. 07/681,118, is a continuation-in-part of U.S. patent application Ser. No. 07/349,304, filed May 9, 1989, now U.S. Pat. No. 5,091,343, and said U.S. patent application Ser. No. 07/342,189, filed Apr. 24, 1989, now U.S. Pat. No. 5,116,575. U.S. patent application Ser. No. O7/349,304, filed May 9, 1989, now U.S. Pat. No. 5,091,343 is a continuation-in-part of U.S. patent application Ser. No. 140,388, filed Jan. 4, 1988, now U.S. Pat. No. 4,892,706. U.S. patent application Ser. No. 07/342,189, filed Apr. 24, 1989, now U.S. Pat. No. 5,116,575 is a continuation-in-part of U.S. patent application Ser. No. 229,917, filed Aug. 8, 1988, now U.S. Pat. No. 5,077,008, which is a continuation-in-part of said U.S. patent application Ser. No. 140,388, filed Jan. 4, 1988, now U.S. Pat. No. 4,893,706, and U.S. patent application Ser. No. 07/165,189, now U.S. Pat. No. 5,037,623, filed Mar. 27, 1988, which in turn are continuations-in-part of U.S. patent application Ser. No. 826,730, filed Feb. 6, 1986, now U.S. Pat. No. 4,731,222.

BACKGROUND OF THE INVENTION

The present invention relates to microbial decontamination arts. It finds particular application in conjunction with powdered sterilant concentrates which react in room temperature water to form microcidally active compositions with an extended period of active life for field medical use and will be described with particular reference thereto. It is to be appreciated that the invention will also find application in conjunction with other anti-microbial applications including biocidal compositions for use at elevated temperatures, biocidal compositions with other preselectable active durations, and the like.

Our earlier U.S. Letters Pat. No. 5,116,575 describes a powdered anti-microbial composition which is ideally suited for use in automated liquid sterilization systems such as illustrated in the above-referenced U.S. Pat. No. 4,892,706 or 5,217,698. The anti-microbial composition included two components which reacted in the presence of water to form a strong oxidant- Preferably, acetylsalicylic acid and a perborate, such as sodium perborate, reacted to form peracetic acid. The powdered components further included anti-corrosive materials and buffers. The anti-corrosive materials inhibited corrosion of brass, copper, aluminum, steel, and other materials commonly found in medical, dental, and surgical instruments. The buffers controlled the chemical reaction and assisted in the corrosion inhibition. In particular, the preferred composition was formulated for optimum efficiency at 50° C. and to produce and maintain a peak peracetic acid concentration for the duration of the automated cycle, on the order of ½ hour.

Although the prior formulations were effective for their intended purpose, there is also a need for an antimicrobial formulation which reacts quickly in room temperature water, about 25° C., to produce an antimicrobially active solution for an extended period, on the order of eight hours. Such formulation should also inhibit corrosion and buffer pH to an optimal range.

An article by Death and Coates in the Journal of Clinical Pathology, Vol. 32, pp. 148–153 (1979) entitled "Effective pH on Sporicidal and Microbicidal Activity of Buffered Mixtures of Alcohol and Sodium Hypochlorite" noted superior microbicidal activity in a methanol/hypochlorite mixture and hypochlorite alone when buffered to a pH of about 7.6–8.1. An article by Melicherčíková in the Journal of Hygiene, Epidemiology, Microbiology, and Immunology, Vol. 33, No. 1, pp. 19–28 (1989) entitled "Disinfectant Effect of Persteril in Combination With Detergents" investigated shelf life of Perstil stabilized peracetic acid aqueous solutions. They proposed that peracetic acid should not be applied in combination with basic detergents because the sporicidal effect of peracetic acid was markedly declined at a pH of 9. In a paper by Hauthal, et al. in Tenside Surf. Det., Vol. 27, No. 3, pp. 187–193, entitled "Studies Concerning the Mechanism of Bleaching Activation", the effects of pH on bleaching activators diacetyl dioxohexahydrotriazine (DADHT) and tetraacetyl ethylene-diamine (TAED) in the formation of peroxyacetic acid with hydrogen peroxide or sodium perborate is investigated. This article notes that at higher pH values, the rate of peroxyacetic acid formation increases but becomes unstable, decomposing more rapidly to oxygen and acetic acid.

Although these references address the effects of pH, none teach or fairly suggest an appropriate powdered formulation which mixes in room temperature water to form microcidally effective concentrations of peracetic acid rapidly but whose stability is sufficiently high that microbicidal activity for a period of at least eight hours is assured. The present invention provides a new and improved sterilant formulation which overcomes the abovereferenced problems and others.

SUMMARY OF THE INVENTION

In accordance with the present invention, a powdered mixture of a perborate, a rapid acetylating agent, a slow acetylating agent, and a buffer is provided.

In accordance with a more limited aspect of the present invention, the buffer buffers the pH of a solution formed when the composition is mixed with water to a pH of between 7.5 and 9 and a temperature of 10°–60° C., preferably 25° C.

In accordance with another more limited aspect of the present invention, the rapid acetylating agent includes acetylating agents which produce at least two acetyl groups and the slow acetylating agents includes activators which produce at least a single acetyl group.

In accordance with a more limited aspect of the present invention, the rapid acetylating agent includes TAED and the slow acetylating agent includes acetylsalicylic acid.

In accordance with a still more limited aspect of the present invention, the buffers buffer the pH to a pH below 8.5.

In accordance with a still further aspect of the present invention, additional buffers enter the solution near a peak of peracetic acid production to reduce the pH closer to a neutral pH for greater long term stability.

One advantage of the present invention is that it provides a composition which is mixable with available room temperature water to form an effective liquid microbicide.

Another advantage of the present invention is that the resultant microbicide is stable and effective for an extended duration. This eliminates precise period of use criticality and facilitates use by less-skilled technicians.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

A two compartment packet holds a powdered formulation including a perborate in one compartment and acetylizing agents in the other compartment. The compartments further hold a buffer for buffering the pH, anti-corrosive materials, surfactants, sequestering agents, and the like.

Figure 1:
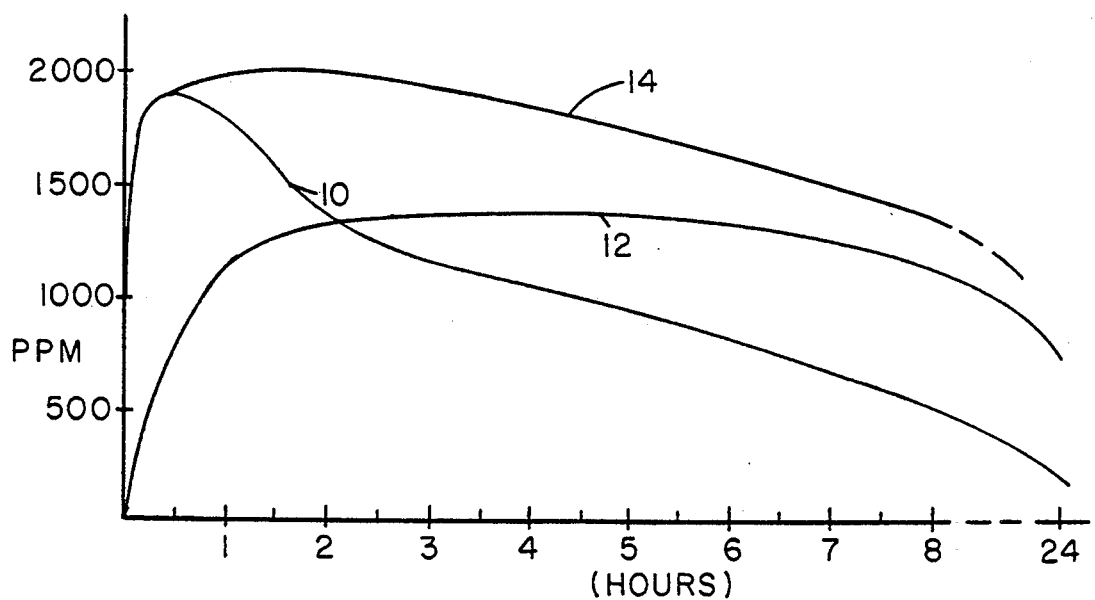
FIG. 1 is a diagrammatic illustration of parts per million of peracetic acid versus time for TAED, acetylsalicylic acid, and a blend of TAED and acetylsalicylic acid.

The acetylizing agent includes a relatively rapid acetylizing agent, i.e. one producing two or more acetyl groups such as TAED. Preferably, the powdered TAED is a methylcellulose encapsulated form of TAED sold under the trademark MYKON TM. As illustrated in curve 10 of FIG. 1, the TAED and the perborate, such as a sodium perborate, react quickly in water to form a microcidally effective concentration of peracetic acid, e.g. 2000 ppm. However, the concentration of peracetic acid tends to decrease relatively rapidly with time. On the other hand, as illustrated by curve 12, acetylsalicylic acid, a slower acetylating agent which produces only a single acetyl group, requires a relatively long duration to reach a maximum peracetic acid concentration. However, the peracetic acid produced with the acetylsalicylic acid acetylating agent is more stable and does not break down or degrade as fast. In order to obtain a rapid generation of a microbicidally effective concentration of peracetic acid yet stability over an extended duration, the TAED and the acetylsalicylic acid are mixed, preferably with a 1:1 molar ratio. As illustrated in curve 14, the peracetic acid solution produced from this mixture is more stable and is microbicidally effective over a longer duration than when formed with either the TAED or the acetylsalicylic acid taken alone.

Because 1 mole of TAED produces 2 moles of peracetic acid and 1 mole of acetylsalicylic produces 1 mole of peracetic acid, the preferred embodiment mixes 0.5 moles of TAED with 1 mole of acetylsalicylic acid to achieve the preferred 1:1 molar ratio. Appropriate amounts of sodium perborate, TAED, and acetylsalicylic acid are provided to generate 2,000 ppm peracetic acid or other biocidically effective amounts, in a preselected quantity of water. The composition further includes benzotriazoles or tolytriazoles or other compositions which inhibit copper and brass corrosion in the presence of strong oxidizing compounds. Azoles, benzoates, and other five-membered ring compounds may also prove acceptable as copper and brass corrosion inhibitors. Phosphates provide pH buffering and inhibit brass and iron corrosion. To inhibit the iron and steel corrosion, phosphates are present in a final concentration of at least 1.25% weight by volume in the resultant solution. For effective pH buffering, higher phosphonate concentrations can be provided. Molybdates, chromates, dichromates, tungstates, vanadates, borates, and combinations thereof may be used in place of or in addition to the phosphates for iron and steel corrosion inhibition and for pH buffering.

The powdered composition preferably includes hexametaphosphate or other sequestering agents for controlling calcium and magnesium salt precipitation in hard water. The sequestering agents further remove substance, e.g. cobalt, that inhibit the precursor reaction. Wetting agents or detergents are also present in a concentration to form a 0.001% to 1.0% weight to volume concentration in the resultant solution.

Other acetyl donors are also contemplated, including diacetyl diohexahydratriazina (DADHT), sodium nanonoyl oxygenzene sulfonate, penta acetyl glucose (PAG), and tetra acetyl glycouril (TAG) are also contemplated.

Figure 2:
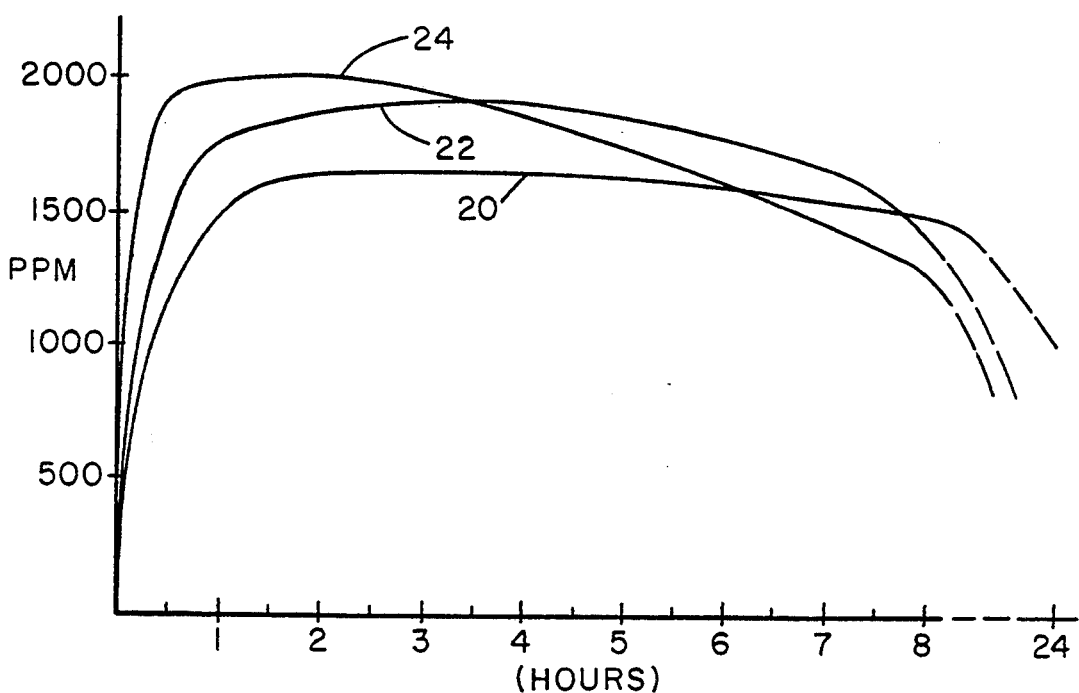
FIG. 2 illustrates parts per million of peracetic acid versus time for a blend of TAED and acetylsalicylic acid buffered to different pHs.

With reference to FIG. 2, pH is observed to have a dramatic effect on the stability and life of the resultant solution. For the 1:1 TAED to acetylsalicylic acid preferred embodiment discussed above, a substantially flat peracetic acid concentration curve 20 is achieved in the range of 1-8 hours for a pH of 8.3. As the pH increases to a pH of 8.51, the production rate of peracetic acid increases but the peracetic acid stability is reduced as illustrated in curve 22. As illustrated by curve when the pH is raised to 8.86, the initial peracetic acid production rate is increased still further, but the resultant solution becomes still more unstable over time.

Figure 3:
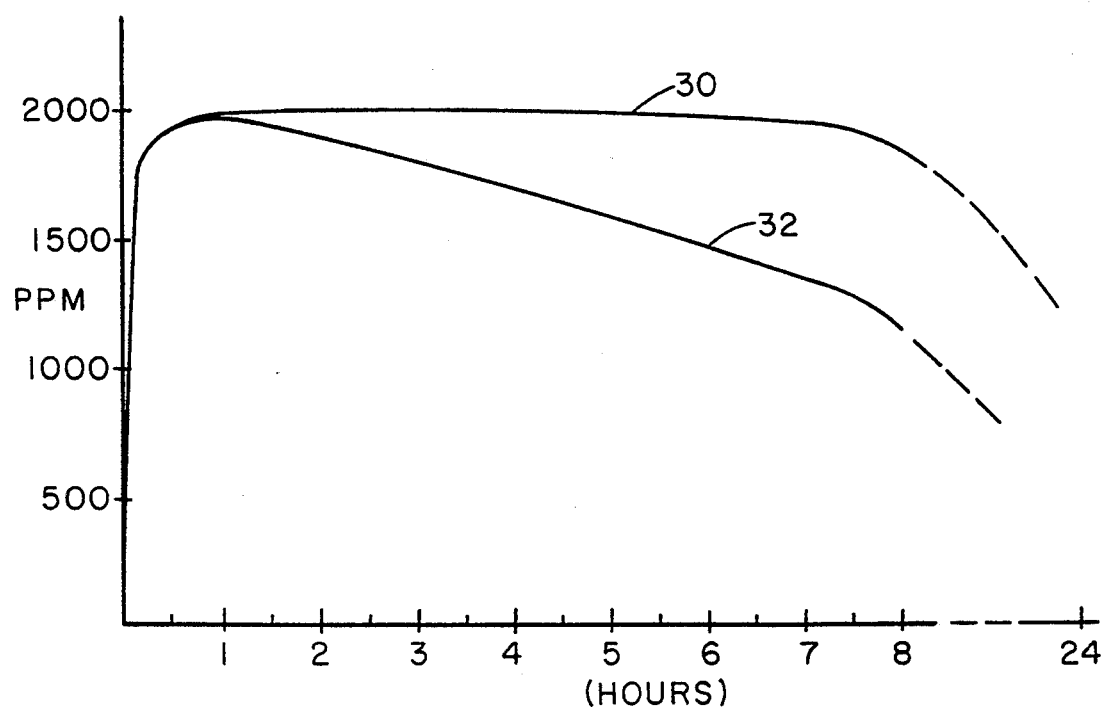
FIG. 3 is a diagrammatic illustration of peracetic acid versus time illustrating the effect of dropping the pH after the peracetic acid is initially formed.

As illustrated in FIG. 3, high pHs are conducive to a rapid production of peracetic acid while lower, more nearly neutral pHs are conducive to long-term stability of the produced peracetic acid. In the embodiment illustrated in FIG. 3, TAED reacts with sodium perborate at a relatively high pH, e.g. pH=8.9, until the peracetic acid concentration approaches a maximum. The pH is then adjusted by adding or otherwise increasing the available amount of buffering agent in the solution. With the pH dropped to about 7.5, as illustrated by curve 30, the peracetic acid concentration remains substantially stable. By distinction, as illustrated in curve 32, when and if the pH is not adjusted and permitted to decrease slowly from 8.9, the peracetic acid concentration decreases reflecting the reduced stability.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A powdered mixture which reacts in water to form peracetic acid in an anti-microbial effective concentration, the powdered mixture comprising:
    a perborate;
    a mixture of a rapid acetyl donor which produces at least two acetyl groups and a slow acetyl donor which produces only a single acetyl group;
    a pH buffer.

2. The mixture as set forth in claim 1 wherein the rapid acetyl donor includes TAED and the slow acetyl donor includes acetylsalicylic acid.

3. The mixture as set forth in claim 1 wherein the slow acetyl donor includes acetylsalicylic acid.

4. The mixture as set forth in claim 3 wherein the rapid acetyl donor is selected from the group consisting of TAED, methyl cellulose encapsulated TAED, tetra acetyl glycouril (TAG), penta acetyl glucose (PAG), and mixtures thereof.

5. The mixture as set forth in claim 4 wherein the acetylsalicylic acid the rapid acetylating agent are present in a 1:1 ratio.

6. The mixture as set forth in claim 4 further including:
    a powdered anti-corrosive material;
    a powdered wetting agent; and
    a powdered sequestering agent for moving substances that inhibit reaction of the perborate and acetyl donors, and for preventing precipitation of calcium and magnesium salts from hard water.

7. The mixture as set forth in claim 6 wherein the anti-corrosive agent is selected from the class consisting of: phosphates, molybdates, chromates, dichromates, tungstates, vanadates, borates, benzotriazoles, tolytriazoles, azoles, benzoates, and combinations thereof.

8. The mixture as set forth in claim 6 wherein the buffering means buffers the resultant peracetic acid solution to a pH between 7.5 and 8.5.

9. The mixture as set forth in claim 1 wherein the buffering agent buffers the pH of the resultant peracetic acid solution to a pH below 9.

10. The mixture as set forth in claim 9 wherein the buffering agent buffers the pH of the resultant peracetic acid solution to a pH between 7.5 and 8.5.

11. The mixture as set forth in claim 1 wherein after peracetic acid concentration has substantially peaked the buffering agent buffers the pH of the resultant peracetic acid solution to a pH of about 7.5.

12. The mixture as set forth in claim 11 wherein the buffering agent permits higher pHs as the peracetic acid concentration is building towards the maximum.

13. A method of microbial decontamination comprising:
    mixing water with a perborate and a rapid acetylating agent which produces at least two acetyl groups and which rapidly causes a short term peracetic acid concentration peak, and with a slow acetylating agent which produces only a single acetyl group and which slowly causes a long term peracetic acid concentration peak, and with a buffer to form a solution with a biocidally effective concentration of peracetic acid;
    immersing an item to be microbially decontaminated in the solution.

14. The method as set forth in claim 13 wherein the rapid acetylating agent includes one of TAED, TAG, and PAG.

15. The method as set forth in claim 14 wherein the slow acetylating agent includes acetylsalicylic acid.

16. The method as set forth in claim 15 wherein the rapid and slow acetylating agents are present in a ratio of substantially 1:1.

17. The method as set forth in claim 15 wherein the resultant solution is buffered to a pH between 7.5 and 8.5.

18. The method as set forth in claim 15 wherein the pH is buffered to a pH greater than 8 during initial peracetic acid formation and after the peracetic acid concentration has substantially reached a peak, reducing the pH of the solution to about 7.5.

19. The method as set forth in claim 18 wherein the mixing step further includes mixing corrosion inhibitors, sequestering agents, and a wetting agent into the solution.

* * * * *

UNITED STATES PATENT AND TRADEMARK OFFICE
CERTIFICATE OF CORRECTION

PATENT NO. : 5,350,563
DATED : September 27, 1994
INVENTOR(S) : Kralovic et al.

It is certified that error appears in the above-indentified patent and that said Letters Patent is hereby corrected as shown below:

Before line 5 of column 1, please insert:

-- LICENSE RIGHTS

The U.S. government has a nonexclusive, nontransferable, irrevocable paid-up license to practice or have practiced this invention for or on its behalf as provided for by the terms of Contract DAMD 17-92-C-2049 awarded by the U.S. Department of the Army. --

Signed and Sealed this

Twenty-third Day of December, 1997

Attest:

BRUCE LEHMAN

*Attesting Officer*       *Commissioner of Patents and Trademarks*